United States Patent
Aso et al.

(10) Patent No.: US 7,855,161 B2
(45) Date of Patent: Dec. 21, 2010

(54) PHOTOCATALYTIC FIBER AND FABRIC USING THEREOF, AND FABRIC PRODUCT USING THE FABRIC

(75) Inventors: Noriyasu Aso, Kawasaki (JP); Masato Wakamura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 12/643,167

(22) Filed: Dec. 21, 2009

(65) Prior Publication Data

US 2010/0112198 A1 May 6, 2010

Related U.S. Application Data

(62) Division of application No. 11/485,450, filed on Jul. 13, 2006, now abandoned.

(30) Foreign Application Priority Data

Mar. 29, 2006 (JP) .............................. 2006-090772

(51) Int. Cl.
| | |
|---|---|
| D02G 3/00 | (2006.01) |
| D02G 3/36 | (2006.01) |
| D02G 3/02 | (2006.01) |
| B32B 27/12 | (2006.01) |
| B32B 27/04 | (2006.01) |
| B32B 5/02 | (2006.01) |
| B32B 27/02 | (2006.01) |
| B32B 17/02 | (2006.01) |
| B32B 19/00 | (2006.01) |
| C01G 23/047 | (2006.01) |
| B01J 23/00 | (2006.01) |

(52) U.S. Cl. ............... 502/300; 502/305; 502/350; 57/7; 57/12; 57/232; 57/236; 57/241; 57/250; 57/400; 442/131; 442/152; 442/164; 442/172; 428/357; 428/364; 428/372; 423/610

(58) Field of Classification Search ............. 502/305, 502/350; 57/7, 12, 232, 236, 241, 250, 400; 442/131, 152, 164, 172; 423/610; 428/357, 428/364, 372
See application file for complete search history.

(56) References Cited

U.S. PATENT DOCUMENTS

2004/0171505 A1 9/2004 Nonami et al.

FOREIGN PATENT DOCUMENTS

JP 08-245208 A 9/1996

(Continued)

*Primary Examiner*—Patricia L Hailey
(74) *Attorney, Agent, or Firm*—Westerman, Hattori, Daniels & Adrian, LLP

(57) ABSTRACT

The purpose of the present invention is to provide a photocatalytic fiber which excels in durability, and decomposition ability against harmful components and can be mass-produced at low cost, a fabric using the fiber, and a fabric product using the fabric. The photocatalytic fiber of the present invention contains a photocatalyst being attached to the fiber. The fiber is preferably having an aspect of forming a thread to which the photocatalyst being attached by spinning after dipping the fiber in a solution at least containing the photocatalyst, an aspect of forming the thread to which the photocatalyst being attached by dipping the fiber in the solution containing at least the photocatalyst after spinning, and an aspect wherein the photocatalyst is a photocatalytic apatite. The fabric of the present invention is characterized by using the photocatalytic fiber. The fabric product of the present invention is characterized by using the fabric.

12 Claims, 2 Drawing Sheets

FOREIGN PATENT DOCUMENTS

| | | | |
|---|---|---|---|
| JP | 2001-302220 A | 10/2001 | |
| JP | 2002-194642 A | 7/2002 | |
| JP | 2002-336705 | * 11/2002 | |
| JP | 2004-052147 A | 2/2004 | |
| JP | 2005-195416 A | 7/2004 | |
| JP | 2005-124777 A | 5/2005 | |
| JP | 2005-177320 A | 7/2005 | |

* cited by examiner

PHOTOCATALYTIC FIBER AND FABRIC USING THEREOF, AND FABRIC PRODUCT USING THE FABRIC

CROSS-REFERENCE TO RELATED APPLICATIONS

This application is a divisional Application of Ser. No. 11/485,450, filed Jul. 13, 2006, which is based on and claims the benefit of priority from Japanese Patent Application No. 2006-090772, filed on Mar. 29, 2006, the entire contents of which being incorporated herein by reference.

BACKGROUND OF THE INVENTION

1. Field of the Invention

The present invention relates to a photocatalytic fiber favorable for forming sanitary materials such as mask, medical cloth, bandage, and gauze, room decorative articles such as curtain, carpet and wall paper, clothing items such as uniform and clothes, livingwares such as towel, sheets and beddings and various filters which excel in decomposition ability of harmful components such as harmful materials or disease agents contained in air, soil and water, a fabric with excellent photocatalytic function using the fiber, and a fabric product using the fabric which is capable of exhibiting excellent photocatalytic function for prolonged period.

2. Description of the Related Art

The sick house syndrome caused by harmful materials such as formaldehyde which are produced from building materials or adhesive bonds used for wall papers in the house has become an issue. As means to remove such harmful materials, for example, a method, in which activated carbon or chemical absorbent is contained in the building materials or wall papers, has been proposed.

It may be possible for the activated carbon or chemical absorbent to absorb harmful materials such as formaldehyde to some extent, however, there is a problem such that the absorption ability relative to the harmful materials gradually fade off and/or disappear after long-term use.

On the other hand, mask use has been drawing an attention as an effective means for protecting against infectious diseases such as cold, influenza, SARS, etc. or measures against allergies to pollen, house dust, etc. The mask has a filter function similar to those of gauze or nonwoven cloth and prevents virus or pollen from invading inside the body by its absorption ability and further parallel use of activated carbon fiber.

It is possible to physically catch disease agents such as bacteria, virus, pollen, etc. in this case, however, it is impossible to kill or inactivate these disease agents and it is difficult to take preventive measures against infectious diseases to perfection.

In recent years, photocatalytic activity (herein after, may be referred to as "photocatalytic function"), which exhibits oxidative decomposition effect, antibacterial effect, antifouling effect, etc., of certain semiconductor materials, e.g. titanium dioxide ($TiO_2$), has been receiving attention to settle above issues. In general, when the semiconductor materials having photocatalytic activity absorb light with an energy corresponding to the band gap between the valence band and the conductor band, the electron present in the valence band transits to the conductor band. The electron which transited to the conductor band have characteristics of moving to substances adsorbed on the surface of the semiconductor material having the photocatalytic activity and, when substances are adsorbed on the surface of the semiconductor material, the substances are reduced by the electron. Due to the transition, a hole is generated in the valence band. The hole generated in the valence band have characteristics of stripping the electron from the substance adsorbed on the surface of the semiconductor material having the photocatalytic activity and, when substances are adsorbed on the surface of the semiconductor material, the substances are oxidized as a result of the strip of the electron thereof by the hole. To explain the above-mentioned phenomenon more specifically, taking titanium dioxide having particularly excellent photocatalytic activity as an example, when titanium dioxide absorbs light with energy equivalent to band gap between the valence band and conduction band, an electron in the valence band of the titanium dioxide transits to the conduction band and the transited electron reduces oxygen in the air, thereby allowing generation of superoxide anion ($.O_2^-$). In contrast, as a result of the transition of the electron, a hole is generated in the valence band and the generated hole allows the generation of hydroxy radical ($.OH$) by oxygenating water adsorbed on the surface of the titanium dioxide. The resulting hydroxy radical is strongly oxidative, and thus when organic substances or the like are adsorbed on the surface of the titanium dioxide, the organic substances or the like are decomposed by the action of the hydroxy radical and finally decomposed to water and carbon dioxide. In this way, when the semiconductor materials having photocatalytic activity, such as titanium dioxide, are exposed to light with an energy equivalent to band gap between the valence band and conduction band of the semiconductor materials, the semiconductor materials absorb the light and organic substances or the like absorbed on the surface are decomposed. Thus, oxidative decomposition effect, antibacterial effect, antifouling effect, etc. are achieved.

Since the titanium dioxide has low absorption ability toward materials, it is often used simultaneously with the absorbent such as activated carbon, and oxidative decomposition effect, antibacterial effect, antifouling effect, etc. are exhibited by decomposing the material absorbed by the absorbent with the titanium dioxide. The titanium dioxide and absorbent are attached to the target (base material) such as mask, etc. by using binders or adhesives.

However, the viruses smaller than the absorbent particle hardly comes in contact with the titanium oxide when they are absorbed by the absorbent, thereby making it difficult to decompose and remove all the material absorbed by the absorbent. Moreover, because the titanium dioxide decomposes organic materials as described above, organic materials are not usable as binders or adhesives and particular kind of binders or adhesives such as inorganic binders must be used. If organic binders, etc. are used, the surface of photocatalyst must be coated with silica in order to avoid direct contact with binders or adhesives. Furthermore, when binders or adhesives are used, photocatalyst is buried inside of these binders or adhesives and the buried portion does not exhibit photocatalytic function, thereby degrading the photocatalytic function and possibly making it uneconomical because of the wasted use of expensive photocatalyst. And also, binders or adhesives may impair the texture of the mask.

Further, a method in which a photocatalyst is contained in the base material by dipping the base material such as mask in a photocatalytic solution without a use of binders, etc. and a method in which photocatalytic solution is sprayed to the base material for adhesion have been performed.

In these cases, however, binding property between the surface of the base material and titanium dioxide is insufficient, and most of the titanium dioxide falls off from the base material by washing, etc., significantly degrading the photocatalytic function. And fibers of the mask, etc. are decomposed by the photocatalytic reaction of the titanium dioxide, degrading the strength.

At the same time, a photocatalytic apatite which has both of photocatalytic function and absorption ability toward materials has been developed as a photocatalyst. It is unnecessary for the photocatalytic apatite to use absorbent simultaneously as for the titanium dioxide because of its excellent absorption property. Moreover, since decomposition of fiber does not occur, any binders or adhesives can be used and there is no need for the surface to be coated with silica.

The methods for attaching the photocatalytic apatite to the base material such as a method in which a base material such as mask is dipped in a photocatalytic solution as similar to the titanium dioxide (Japanese Patent Application Laid-Open (JP-A) No. 2005-177320) and a method in which the photocatalytic apatite is attached to the base material by using binders or adhesives (JP-A No. 2005-124777) have been disclosed. In the invention disclosed in JP-A No. 2005-124777, a method for preventing dropout of the photocatalytic apatite from the base material by disposing a protective layer on the surface of the base material to which the photocatalytic apatite is attached is further disclosed.

In this case, however, when binders or adhesives are used for adhesion to the base material, photocatalytic apatite is buried in these binders or adhesives, resulting in degraded photocatalytic function and making it uneconomical. And also, when binders, etc. are used, or when the photocatalytic apatite is attached by dipping, the photocatalytic apatite is attached only to the surface of the base material, and a problem still remains such that the photocatalytic apatite is likely to fall off by washing.

Therefore, an appropriate proposal of the product such as mask which excels in durability without impairment of the strength or texture of the base material, excels in decomposition ability against the harmful components such as harmful materials or disease agents contained in air, soil and water, is capable of exhibiting excellent photocatalytic function for prolonged period and can be mass-produced at low cost, has not been provided in the existing situation.

The present invention is intended to settle above existing issues and achieve the following purposes.

The purpose of the present invention is to provide a photocatalytic fiber which excels in durability, and decomposition ability against the harmful components such as harmful materials or disease agents contained in air, soil and water, can be mass-produced at low cost, and is favorable for forming sanitary materials such as mask, medical cloth, bandage, and gauze, room decorative articles such as curtain, carpet and wall paper, clothing items such as uniform and clothes, livingwares such as towel, sheets and beddings and various filters. Also provided is a fabric which excels in photocatalytic function and durability, can be mass-produced at low cost and is favorable for forming sanitary materials such as mask, medical cloth, bandage, and gauze, room decorative articles such as curtain, carpet and wall paper, clothing items such as uniform and clothes, livingwares such as towel, sheets and beddings and various filters by using the fiber. And also provided is a fabric product including sanitary materials such as mask, medical cloth, bandage, and gauze, room decorative articles such as curtain, carpet and wall paper, clothing items such as uniform and clothes, livingwares such as towel, sheets and beddings and various filters which can exhibit excellent photocatalytic function for prolonged period.

As a result of dedicated investigation conducted on the issues, the present inventors have obtained the following knowledge. It has been found that by using the photocatalytic apatite as a photocatalyst, an excellent photocatalytic function can be obtained without degrading the fiber even if it is directly attached to the fiber. Moreover, it has been found that by attaching the photocatalyst to the fiber forming the fabric for forming a mask, etc. and forming the fabric with the fiber, instead of attaching the photocatalyst on the surface of the base material, a solid binding property between the fabric and the photocatalyst can be obtained without a use of binders, etc. because the photocatalyst can be physically fixed in meshes or crossings of the fiber.

SUMMARY OF THE INVENTION

The present invention is based on the knowledge of the present inventors and the measures to settle above issues are as follows.

The photocatalytic fiber of the present invention contains a photocatalyst wherein the photocatalyst is attached to the fiber.

In the fiber, the harmful components or decomposition targets contained in air, soil and water are decomposed and removed by the photocatalyst because the photocatalyst is attached to the fiber. By attaching the photocatalyst without a use of binders or adhesives, photocatalyst is not buried in the binders, etc. and the surface of the photocatalyst is externally exposed thereby efficiently bringing out the photocatalytic function. Moreover, it is possible to mass-produce the fiber with excellent photocatalytic function at low cost, and the fiber having an excellent durability is obtained without impairing strength or texture of the fiber. Therefore, it is favorably used for fabric products of the present invention using the fabric of the present invention.

The fabric of the present invention is formed by using the photocatalytic fiber of the present invention.

In the fabric of the present invention, the harmful components contained in air, soil and water are decomposed and removed by the photocatalyst attached to the fabric because it is formed by using the photocatalytic fiber of the present invention.

Heretofore, photocatalyst has been attached to the mask, etc. by using binders or adhesives and the photocatalyst is buried in the binder, etc. having less contact with the harmful components, and therefore photocatalytic function cannot be exhibited sufficiently. Furthermore, texture of mask, etc. has been impaired by the binders, etc. And when the photocatalyst is attached by dipping masks, etc. in a photocatalytic solution or by spraying the photocatalytic solution without using binders, etc., binding property of the photocatalyst and mask is inappropriate and since the photocatalyst attaches only on the surface of the masks, etc., there is a problem of notably degraded photocatalytic function because most of the photocatalyst falls off by washing. Moreover, when titanium dioxide is used as a photocatalyst and is directly attached to the masks, etc. there is a problem of decreased strength due to decomposition of the fiber by photocatalytic reaction.

Since the fabric of the present invention is formed by using the fiber to which the photocatalyst is attached in advance, the fiber is crossed and tangled with each other and the photocatalyst is held in meshes or crossings of the fiber to improve the binding property of the fabric and the photocatalyst. Moreover, a lot of photocatalyst can be attached not only on the surface of the fabric but inside the fabric. And because of the excellent binding property, photocatalyst can be attached without a use of binders or adhesives, etc. thereby increasing the contact area with harmful components and preventing the impairment of strength and texture, etc. of the fabric. Moreover, it is possible to appropriately prevent degradation of the fiber by using photocatalytic apatite. As a result, a fabric which is capable of exhibiting excellent photocatalytic function can be mass-produced at low cost. Further, photocatalyst does not fall off easily even by washing, and a fabric which excels in durability and is capable of exhibiting excellent photocatalytic function for prolonged period can be obtained. Because of this, the fabric is favorably used for the fabric product of the present invention.

The fabric product of the present invention is formed by using the fabric of the present invention.

Since the fabric product is formed by using the fabric of the present invention, mass production at low cost is possible, and harmful components contained in air, soil and water are decomposed and removed by photocatalyst attached to the fabric product. Furthermore, photocatalyst does not fall off easily even by washing, the strength and the texture of the fabric product are not impaired and it is possible for the fabric product to exhibit excellent photocatalytic function for prolonged period with an excellent durability. Therefore, the fabric product of the present invention can be favorably used for sanitary materials such as protective mask, antidust mask, antibromic mask, sporting mask, medical cloth, bandage, and gauze, room decorative articles such as curtain, carpet and wall paper, clothing items such as uniform and clothes, livingwares such as towel, sheets and beddings and various filters.

DESCRIPTION OF THE PREFERRED EMBODIMENTS

Photocatalytic Fiber

Figure 1:
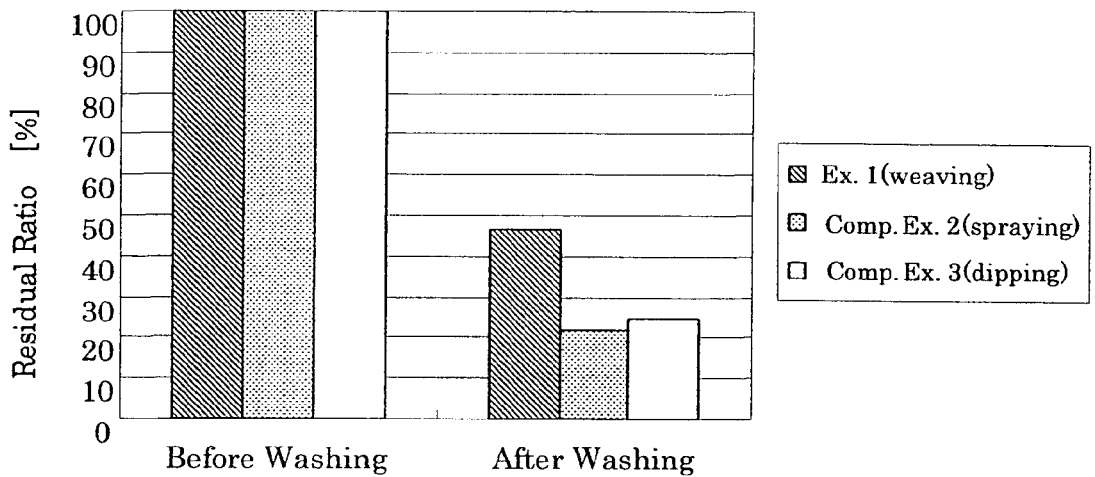
FIG. 1 is a graph showing a measurement result of the photocatalyst adhesive strength of Example 1 which uses a cotton fabric formed of the photocatalytic fiber of the present invention, Comparative Example 2 which uses a cotton fabric to which photocatalyst is attached by spraying, and Comparative Example 3 using a cotton fabric to which photocatalyst is attached by dipping.

The photocatalytic fiber of the present invention contains a photocatalyst attached to the fiber and further contains other constituents appropriately selected accordingly.

—Fiber—

The material of the fiber is not particularly limited and may be selected accordingly. Examples include cotton, hemp, silk, coat, pulp, synthetic fiber and regenerated fiber and of these, cotton is preferable. These may be used alone or in combination.

The structure of the fiber is not particularly limited and may be selected accordingly. For example, it may be a short fiber such as cotton, coat and pulp or a long fiber such as silk and synthetic resin. Moreover, it may be a thread formed by spinning the short fibers or a thread formed by spinning the long fibers.

The method for attaching photocatalyst to the fiber is not particularly limited and may be selected accordingly and examples include a method in which photocatalyst is dispersed in a solvent such as water to prepare a photocatalytic solution and photocatalyst is attached by dipping the fiber in the photocatalytic solution and drying, and a method for attaching using static electricity.

Further, the method for attaching photocatalyst to the fiber include a method for forming threads to which the photocatalyst is attached by twisting the fiber after a fiber such as short fiber and long fiber is dipped in the photocatalytic solution such as above and dried, and a method for forming threads to which the photocatalyst is attached by spinning the fiber in advance and then dipping the fiber in the photocatalytic solution and drying.

By spinning as described above, the photocatalyst can be physically fixed in the thread crossings or fiber meshes and binding property of fiber and photocatalyst is improved.

In particular, by using photocatalytic apatite as a photocatalyst, degradation of fiber can be prevented even if the photocatalyst is attached directly to the fiber, and excellent durability can be obtained.

—Photocatalyst—

The embodiment of the photocatalyst is not particularly limited and its form, structure, size and specific gravity can be suitably selected. For example, the photocatalyst is preferably in form of particle (grain), powder and porous solid. Of these, powdery form is particularly preferable in terms of appropriate adhesive property with the fiber.

The size of the photocatalyst is not particularly limited and may be selected according to the width and length, etc. of the fiber. For example, when the photocatalyst is in form of powder and/or particle (grain), the average particle diameter of the photocatalyst is preferably 3 μm to 8 μm.

Examples of the structure of photocatalyst include single layer structure, multiple layer structure, porous structure and core-shell structure.

The specific gravity of the photocatalyst is not particularly limited and may be selected accordingly and it is preferably small.

When the photocatalyst is in form of powder, the particle size distribution of the photocatalyst is not particularly limited and may be selected accordingly. For example, as the particle size distribution becomes sharp or narrow, the photocatalyst can be dispersed evenly in the fiber.

Meanwhile, observation of the identification and embodiment of the photocatalyst can be performed by TEM, XRD, XPS, FT-IR, etc. for example.

The light wavelength necessary for exhibiting photocatalytic activity of the photocatalyst is not particularly limited and may be selected accordingly. It is preferably having an absorption property and capable of exhibiting photocatalytic activity relative to the broadband light including ultraviolet light and/or visible light.

The adhesive amount of the photocatalyst relative to the fiber is not particularly limited and may be adjusted accordingly. As the adhesive amount of the photocatalyst increases, the decomposition ability against harmful components (decomposition targets) improves, however, binding property with the fiber is degraded, and therefore it is preferable that the content is increased to an extent that it is capable of shape forming. For example, it is preferably 0.001 parts by mass to 50 parts by mass and more preferably 0.01 parts by mass to 30 parts by mass relative to 100 parts by mass of the fiber.

The material and/or composition of the photocatalyst are not particularly limited and may be selected accordingly and preferred examples include apatite having photocatalytic activity (photocatalytic function). When the photocatalyst is an apatite having photocatalytic activity, it is advantageous in terms of excellent absorption property of apatite relative to the harmful components contained in air, soil and water, etc. Moreover, it is advantageous in terms of being capable of decomposing and removing absorbed harmful components efficiently by its photocatalytic activity (photocatalytic function).

Of these photocatalysts, a photocatalyst at least containing apatite having photocatalytic activity and visible light-absorbing metal atom is preferable and a photocatalyst further containing ultraviolet-absorbing metal atom is more preferable. If the photocatalyst contains the visible light-absorbing metal atom, it is advantageous for use under conditions of daily usage with fluorescent lamp. And if it further contains ultraviolet-absorbing metal atom, it is advantageous for use under irradiation condition of light including ultraviolet light such as sun light.

Meanwhile, the photocatalyst may be used alone or in combination in the present invention.

The visible light-absorbing metal atom is not particularly limited and may be selected accordingly. Preferred examples include the visible light-absorbing metal atom having absorption property relative to the light of 400 nm wavelength or more and specifically, at least one selected from chromium (Cr) and nickel (Ni) is more preferable.

The apatite having photocatalytic activity (photocatalytic function) is not particularly limited as long as it has a photocatalytic activity and may be selected accordingly. Preferred examples include an apatite containing a metal atom necessary for obtaining a photocatalytic activity (herein after, may be referred to as "metal atom capable of exhibiting photocatalytic activity"). The apatite can strip electrons from the harmful components (decomposition targets) absorbed on the surface of apatite and oxygenate and decompose the harmful components when the apatite contains the metal atom necessary for obtaining photocatalytic activity.

The apatite is not particularly limited and may be selected accordingly. Examples include the apatite expressed by the following General Formula (I).

   General Formula (I)

In the above General Formula (I), "A" represents a metal atom and the metal atom is not limited and may be selected accordingly. Examples of the metal atom include calcium (Ca), aluminum (Al), lanthanum (La), magnesium (Mg), strontium (Sr), barium (Ba), lead (Pb), cadmium (Cd), europium (Eu), yttrium (Y), cerium (Ce), sodium (Na) and potassium (K). Of these, calcium (Ca) is particularly preferable in terms of excellent absorption property.

"B" represents one of phosphorus atom (P) and sulfur atom (S) and of these, phosphorus atom (P) is preferable in terms of excellent biocompatibility.

"O" represents an oxygen atom.

"X" represents one of hydroxyl group (OH), $CO_3$ and halogen atom and of these; hydroxyl group (OH) is particularly preferable because it is capable of forming metal-oxide photocatalytic substructure together with the metal atom A. Examples of halogen atom include fluorine atom, chlorine atom, bromine atom and iodine atom.

Each "m", "n", "z" and "s" represents an integer and "m" is preferably 8 to 10, "n" is preferably 3 to 4, "z" is preferably 5 to 7 and "s" is preferably 1 to 4 in terms of appropriate charge balance, for example.

Examples of the apatite expressed by the above General Formula (I) include hydroxyapatite, fluoroapatite, chloroapatite, or metallic salt thereof, tricalcium phosphate or calcium hydrogen phosphate. Of these, it is preferably hydroxyapatite where "X" in the above General Formula (I) is a hydroxyl group (OH) and it is more preferably calcium hydroxyapatite (CaHAP), that is, $Ca_{10}(PO_4)_6(OH)_2$ where "A" is calcium (Ca), "B" is phosphorus atom (P), and "X" is a hydroxyl group (OH) in the above General Formula (I).

Since the calcium hydroxyapatite (CaHAP) is liable to undergo ion exchange with cation as well as anion, it excels in absorption properties relative to various harmful components (decomposition targets) in particular, organic substances such as protein and in addition, it excels in absorption properties relative to microscopic organisms such as viruses, fungi and bacteria, thereby preventing or inhibiting the propagation thereof.

The decomposition target is not particularly limited and may be selected accordingly. Examples of constituents thereof include proteins, amino acids, lipids and carbohydrates. The decomposition target may contain one or two or more of these. Specific examples of the decomposition target generally include dirt derived from human skin, dirt, dust, sludge, unwanted components, waste fluid components, harmful substances in the soil and/or air, disease agents such as microorganisms and viruses. Examples of the harmful substances include tar component, acetaldehyde gas (formaldehyde released from wall paper, etc. and acetaldehyde contained in smoke such as tobacco, etc.) and phenol components (phenol contained in smoke, etc.).

The microorganisms are not particularly limited and may be any one of prokaryote and eukaryote and also include protozoan. Examples of prokaryote include bacteria such as *Escherichia coli* and *Staphylococcus aureus* and examples of eukaryote include yeast, and mould fungi such as fungus and antinomyces. Moreover, pollens of cedar, Japanese cypress, hogweed and others are also included.

Examples of virus include DNA virus and RNA virus and in particular, influenza virus and SARS virus.

These decomposition targets may be contained in air, soil or water singly, or two or more of these may be contained simultaneously.

These decomposition targets may exist in any embodiment of solid, liquid and vapor. Examples of the decomposition targets in liquid form include waste fluid, nutrient fluid and circulation fluid. Examples of the decomposition targets in vapor form include air, exhaust gas and circulation gas.

The content of apatite in the photocatalyst is not particularly limited and may be adjusted accordingly. For example, it is preferably 85 mol % to 97 mol % and more preferably 85 mol % to 90 mol %.

When the content of apatite is less than 85 mol %, the photocatalytic activity of the photocatalyst may not be sufficient, and even when it is more than 97 mol %, appropriate effect may not be obtained and absorption property and photocatalytic activity of the photocatalyst relative to the harmful components (decomposition targets) may be degraded.

Meanwhile, the content of apatite in the photocatalyst can be, for example, measured by performing quantitative analysis by ICP-AES.

The metal atom necessary for obtaining the above photocatalytic activity is not particularly limited as long as it can function as a center of photocatalyst and may be selected from known metal atoms having photocatalytic activity accordingly. For example, at least one suitably selected from titanium (Ti), zinc (Zn), manganese (Mn), tin (Sn), indium (In) and iron (Fe) is preferable for its excellent photocatalytic activity. Of these, titanium (Ti) is preferable for its excellent photocatalytic activity (photocatalytic function) in particular.

The content of metal atom necessary for obtaining photocatalytic activity is not particularly limited and may be adjusted accordingly. For example, it is preferably 5 mol % to 15 mol % and more preferably 8 mol % to 12 mol % relative to the total metal atom in the photocatalyst.

If the content of the metal atom necessary for obtaining photocatalytic activity is less than 5 mol %, photocatalytic activity of the photocatalyst may not be satisfactory and even when it is more than 15 mol %, appropriate effect may not be obtained and moreover, absorption property or photocatalytic activity of the photocatalyst relative to decomposition targets may be degraded.

Meanwhile, the content of the metal atom necessary for obtaining photocatalytic activity can be, for example, measured by performing quantitative analysis by ICP-AES.

The metal atom necessary for obtaining photocatalytic activity are incorporated (e.g., by substitution) into the crystal structure of the apatite as part of metal atoms constituting the crystal structure of the apatite in order to form a "photocatalytic substructure" which is capable of exhibiting photocatalytic function in the crystalline structure of the apatite.

The apatite having such photocatalytic substructure has photocatalytic activity, and excels in decomposition effect, antibacterial effect, antifouling effect and inhibition and/or reduction of propagation of fungi, bacteria, etc. because the apatite structure segment excels in absorption property and excels more in absorption property relative to the harmful components (decomposition targets) than the known metal oxides having photocatalytic activity.

Specifically, the photocatalyst is preferably having titanium (Ti) as the metal atom necessary for obtaining photocatalytic activity and calcium hydroxyapatite (CaHAP): $Ca_{10}(PO_4)_6(OH)_2$ as the apatite.

The photocatalyst as described above excels in absorption performance of the harmful components (decomposition targets) contained in air, soil and water, etc.

An appropriately synthesized apatite or commercially available apatite may be used as apatite having photocatalytic activity.

The method for synthesizing apatite having photocatalytic activity is not particularly limited and may be selected accordingly. For example, the apatite may be synthesized by doping the metal atom necessary for obtaining photocatalytic activity in the apatite.

The preferred examples of titanium-calcium hydroxyapatite as a commercially available apatite having photocatalytic activity include "PHOTOHAP P CAP-100" manufactured by Taihei Chemical Industrial Co., Ltd.

The aspect of doping is not particularly limited and may be selected accordingly. Examples include substitution, chemical bonding and absorption and of these, substitution is preferable because reaction is easily controllable, and metal atom necessary for obtaining photocatalytic activity can be held stably in the photocatalyst without detachment after doping.

The aspect of substitution is not particularly limited and may be selected accordingly. For example, an aspect in which at least a part of metal atom in the apatite is substituted with the metal atom necessary for obtaining photocatalytic activity and an aspect in which at least a part of the metal atom is substituted with the visible light-absorbing metal atom are preferable. These aspects are better for holding atoms necessary for obtaining photocatalytic activity in the apatite without detachment.

The types of substitution with the metal atom necessary for obtaining photocatalytic activity are not particularly limited and may be selected accordingly and preferred examples include ion exchange, etc. When ion exchange is employed as substitution, it is advantageous in terms of excellent substitution efficiency.

The specific method for doping, that is, the specific method for doping the metal atom necessary for obtaining photocatalytic activity in the apatite is not particularly limited and may be selected accordingly. For example, dipping method in which the apatite is dipped in a water solution where compounds including the metal atom necessary for obtaining photocatalytic activity, etc. are dissolved or coexist, and coprecipitation method in which raw materials of the apatite and the metal atom necessary for obtaining photocatalytic activity are coprecipitated in a water solution where compounds including the raw materials of the apatite and the metal atom necessary for obtaining photocatalytic activity, etc. are dissolved or coexist, are preferable.

Meanwhile, the water solution may be left at rest; however, it is preferable to stir the solution for more efficient substitution to take place. The solution may be stirred by means of known equipments and units and examples include magnetic stirrer and stirring apparatus.

Of these methods, dipping method is more preferable because it can be easily operated.

In dipping method, the apatite may be dipped in a water solution where the metal atom necessary for obtaining photocatalytic activity is dissolved or coexist, or compounds including the metal atom necessary for obtaining photocatalytic activity may be dissolved in a water solution in which the apatite has been dispersed.

The density of the apatite in the water solution during doping is not particularly limited and may be adjusted accordingly. For example, it is preferably 0.3% by mass to 1.0% by mass and more preferably 0.4% by mass to 0.6% by mass.

When the density of the apatite is less than 0.3% by mass, photocatalytic activity may be degraded and even when it is more than 1.0% by mass, appropriate enhancing effect of photocatalytic activity may not be obtained and photocatalytic activity may be degraded.

The density of the metal atom necessary for obtaining photocatalytic activity in the water solution during doping is not particularly limited and may be adjusted accordingly. For example, it is preferably $1 \times 10^{-4}$M to $1 \times 10^{-3}$M and more preferably $1 \times 10^{-4}$M to $5 \times 10^{-4}$M.

When the density of the metal atom necessary for obtaining photocatalytic activity is less than $1 \times 10^{-4}$M, photocatalytic activity may be degraded, and even when it is more than $1 \times 10^{-3}$M, appropriate enhancing effect of photocatalytic activity may not be obtained and photocatalytic activity may be degraded.

The reaction system for doping is not particularly limited and may be selected accordingly. The reaction may take place in liquid and air, for example, and it is preferably performed in liquid. The liquid in this case is not particularly limited and may be selected accordingly and it is preferably water and/or liquid mainly consisting of water.

The container containing the liquid is not particularly limited and may be selected from known containers. The preferred examples include mixer and stirrer in large scale and beaker in small scale.

The doping condition is not particularly limited and the temperature, time and pressure, etc. may be selected accordingly.

The temperature is not particularly limited and it differs depending on the type and mass ratio of the material and cannot be defined completely. Normally, it is approximately 0° C. to 100° C. and preferably at room temperature (20° C. to 30° C.), for example. The doping time is not particularly limited and it differs depending on the type and mass ratio of the material and cannot be defined completely. Normally, it is approximately 10 seconds to 30 minutes and preferably 1 minute to 10 minutes. The pressure is not particularly limited and it differs depending on the type and mass ratio of the material and cannot be defined completely. It is preferably atmospheric pressure.

The amount of the metal atom necessary for obtaining photocatalytic activity in the photocatalyst can be controlled as desired, by appropriately adjusting the additive amount (M) or the above condition.

The sintering is a step for sintering the apatite, which has been doped with the metal atom necessary for obtaining photocatalytic activity, at 600° C. to 800° C. after doping is completed.

When the sintering temperature is less than 600° C., photocatalytic activity may not be at its maximum, and when it is more than 800° C., decomposition may occur.

The sintering condition such as time, atmosphere, pressure and equipment, etc. for example, is not particularly limited and may be selected accordingly. The sintering time depends on the amount of apatite which has been doped and cannot be defined completely; however, it is preferably more than 1 hour and more preferably 1 hour to 2 hours, for example. Examples of the atmosphere include inert gas atmosphere such as nitrogen and argon, and atmospheric air, and it is preferably atmospheric air. Examples of the pressure include atmospheric pressure. And known sintering apparatuses may be used as the equipment.

By sintering, the crystalline state of the apatite, which has been doped with the metal atom necessary for obtaining photocatalytic activity, may be improved and photocatalytic function including absorption properties and photocatalytic activity of the photocatalyst may be further improved.

An example of the method for manufacturing the photocatalyst will be explained. When the doping is performed by substitution, in particular, when the substitution is performed by ion exchange by dipping, a titanium sulfate solution containing titanium as the metal atom necessary for obtaining photocatalytic activity is prepared first. The apatite, calcium hydroxyapatite (CaHAP) is weighed in a beaker to which the titanium sulfate solution is added. After stirring the mixed solution by means of a magnetic stirrer for 5 minutes, a suction filtration is performed with filter paper by means of an aspirator, and TiHAP fine particles which have been doped with titanium are obtained by washing with pure water and drying in an oven at 100° C. for 2 hours. Afterward, it is baked in a muffle furnace at 650° C. for 1 hour in an atmospheric air. As described above, the photocatalyst which contains TiHAP fine particles, which have been doped with titanium as the metal atom necessary for obtaining photocatalytic activity, (the apatite having the metal atom necessary for obtaining photocatalytic activity) is produced.

—Other Constituents—

Other constituents which are attached to the fiber are not particularly limited and may be selected accordingly. It is possible to attach fragrant materials, antibacterial agents and medical agents in the case of masks, filters, medical fabrics and clothes.

The fiber of the present invention is favorably used in various fields because it has an excellent durability and decomposition ability against harmful components such as harmful materials or disease agents contained in air, soil and water, and can be mass-produced at low cost. For example, it is favorably used for sanitary materials such as mask, medical cloth, bandage, and gauze, room decorative articles such as curtain, carpet and wall paper, clothing items such as uniform and clothes, livingwares such as towel, sheets and beddings and various filters in particular, and for the fabric of the present invention and the fabric product of the present invention using the fabric respectively in particular.

(Fabric)

The fabric of the present invention is formed by using the photocatalytic fiber of the present invention.

The embodiment of the fabric is not particularly limited and may be selected accordingly and it may be woven cloth, nonwoven cloth or paper. Of these, woven cloth is preferable for its excellent binding ability with the photocatalyst.

—Woven Cloth—

The woven cloth may be a woven cloth woven with the threads formed with the fiber by means of weaving machines, etc. and may be a cloth knitted with the threads by means of knitting machines, etc.

Since the photocatalyst is physically fixed in meshes formed by multiple threads crossed or tangled in every direction or in thread crossings, solid binding ability with which the photocatalyst does not fall off easily from the woven cloth can be obtained without binders, etc.

—Nonwoven Cloth—

The nonwoven cloth is formed in form of cloth by tangling the fiber instead of knitting or weaving the fiber.

The method for manufacturing the nonwoven cloth is not particularly limited and may be selected accordingly and examples include wet and dry methods. Examples of the wet method include water flow tangling and examples of the dry method include span bonding, thermal bonding and needle punch.

The photocatalyst is fixed in meshes and binding parts formed by intricately tangled fibers in the nonwoven cloth, solid binding ability with which the photocatalyst does not fall off easily from the nonwoven cloth can be obtained.

—Paper—

The paper is not particularly limited and may be selected accordingly and in particular, it is preferably Japanese paper.

The method for manufacturing the paper is not particularly limited and may be selected accordingly. For example, it is possible to form Japanese paper with a fiber to which the photocatalyst is attached by pouring a solution containing photocatalyst in a liquid for making paper and attaching the photocatalyst on the fiber of Japanese paper while making paper, enabling an easy production at low cost.

Since the photocatalyst is also fixed in meshes or binding parts formed by intricately tangled fibers, solid binding ability by which the photocatalyst does not fall off easily from the paper can be obtained.

The residual ratio of the photocatalyst in the fabric after washing to the attachment amount of the photocatalyst before washing when the fabric is washed by means of an ultrasonic washing machine for 30 minutes, [attachment amount after washing (g)/attachment amount before washing (g)]×100 is preferably 40% to 100% and more preferably 50% to 100%.

Since the fabric of the present invention is formed by using the fiber to which the photocatalyst is attached in advance, the photocatalyst is fixed between fibers by crossing or tangling of the fibers, thereby improving the binding ability of the fabric and photocatalyst. Moreover, photocatalyst can be attached in large quantity to the inner part of the fabric as well as to the surface of the fabric. And with an excellent binding ability, it is possible to attach without a use of binders or adhesives, allowing an increase in contact area with harmful components and preventing the impairment of the strength and texture of the fabric and also, by using the photocatalyst, fibers are not decomposed. As a result, the fabric which is capable of exhibiting excellent photocatalytic function can be mass-produced at low cost. Moreover, the photocatalyst does not fall off easily even by washing, and the fabric which excels in durability and is capable of exhibiting excellent photocatalytic function for prolonged period can be obtained.

The fabric of the present invention can be favorably used for the fabric products including sanitary materials such as mask, medical cloth, bandage, and gauze, room decorative articles such as curtain, carpet and wall paper, clothing items such as uniform and clothes, livingwares such as towel, sheets and beddings and various filters, and it is favorably used for the fabric product of the present invention in particular.

(Fabric Product)

The fabric product of the present invention is formed by using the fabric of the present invention.

Since the fabric products are formed by using the fabric of the present invention, harmful components contained in air, soil and water are decomposed and removed by the photocatalyst attached to the fabric. Such fabric products which are capable of exhibiting excellent photocatalytic function can be mass-produced at low cost. Furthermore, the photocatalyst does not fall off easily even by washing, the strength and texture of the fabric products are not impaired, enabling to obtain the fabric products which excel in durability and are capable of exhibiting excellent photocatalytic function for prolonged period.

The fabric product of the present invention is favorably used for sanitary materials such as protective mask, antidust mask, antibromic mask, sporting mask, medical cloth, bandage, and gauze, room decorative articles such as curtain, carpet and wall paper, clothing items such as uniform and clothes, livingwares such as towel, sheets and beddings and various filters.

EXAMPLES

Herein below, with referring to Examples and Comparative Examples, the invention is explained in detail and the following Examples and Comparative Examples should not be construed as limiting the scope of this invention.

Example 1

Gauze (Cotton Fabric) Formation

A photocatalytic apatite powder (PHOTOHAP PCAP-100, a titanium-calcium hydroxyapatite manufactured by Taihei Chemical Industrial Co., Ltd.) was dispersed in water to prepare a photocatalytic solution.

A cotton fiber was dipped in the photocatalytic solution and dried to prepare a cotton fiber to which 6.0 mg of the photocatalytic apatite powder was attached. Next, the cotton fiber was weaved to form a cotton fabric of 25 mm×150 mm (in gauze form with 1 mm of mesh spacing) and a sample of Example 1 to which 6.0 mg of the photocatalytic apatite powder was attached was obtained.

Comparative Example 1

A commercially available cotton gauze (with 1 mm of mesh spacing) was provided as a sample of Comparative Example 1 to which the photocatalyst is not attached.

Comparative Example 2

The photocatalytic solution prepared in Example 1 was sprayed over commercially available cotton gauze as similar to the one in Comparative Example 1 and dried to obtain a sample of Comparative Example 2, a cotton fabric of 25 mm×150 mm to which 6.0 mg of the photocatalytic apatite powder was attached.

Comparative Example 3

A commercially available cotton gauze as similar to the one in Comparative Example 1 was dipped in the photocatalytic solution prepared in Example 1 and dried to obtain a sample of Comparative Example 3, a cotton fabric of 25 mm×150 mm to which 6.0 mg of the photocatalytic apatite powder was attached.

Comparative Example 4

A cotton fabric was formed using a cotton fiber to which 6.0 mg of titanium dioxide was attached as similar to Example 1, except for forming the cotton fabric to which the titanium dioxide was attached by changing the photocatalytic apatite to titanium dioxide (ST-21 manufactured by Ishihara Sangyo Kaisha, Ltd.) to prepare a sample of Comparative Example 4, a cotton fabric of 25 mm×150 mm to which 6.0 mg of titanium dioxide was attached.

—Evaluation—

(1) <Measurement of Adhesive Strength of Photocatalytic Apatite>

The mass of each sample (size: 25 mm×150 mm) of Example 1 and Comparative Examples 2 to 3 was measured. Next, each sample was put in a beaker filled with water and washed by means of an ultrasonic washing machine for 30 minutes. After the samples were dried, mass of each sample after washing was measured.

The residual ratio of the photocatalyst in the sample was obtained by the change in the sample mass before and after the ultrasonic washing and calculated from the next equation, (attachment amount after washing/attachment amount before washing)×100 and the residual ratio was evaluated as adhesive strength. Results are shown in FIG. 1.

From the result shown in FIG. 1, it turns out that the residual ratio of the photocatalyst in the sample of Example 1, in which a cotton fabric formed with the photocatalytic fiber of the present invention was used, was larger than those of the samples of Comparative Examples 2 and 3, in which cotton fabrics to which the photocatalyst is attached by conventional spraying or dipping, and the sample of Example 1 had an excellent adhesive strength (binding ability).

(2) <Evaluation of Photocatalytic Activity>

Each sample of Example 1 and Comparative Example 1 (in strip form of 25 mm×150 mm) was put in a container (500 cc) filled with acetaldehyde (10,000 ppm) and 1.0 mW/cm$^2$ (at 365 nm) of ultraviolet light was irradiated by black light. The amount of carbon dioxide produced by ultraviolet light irradiation was measured by using gas chromatography (GS-560 manufactured by GL Sciences, Inc.) and photocatalytic activity was evaluated. Results are shown in FIG. 2.

Figure 2:
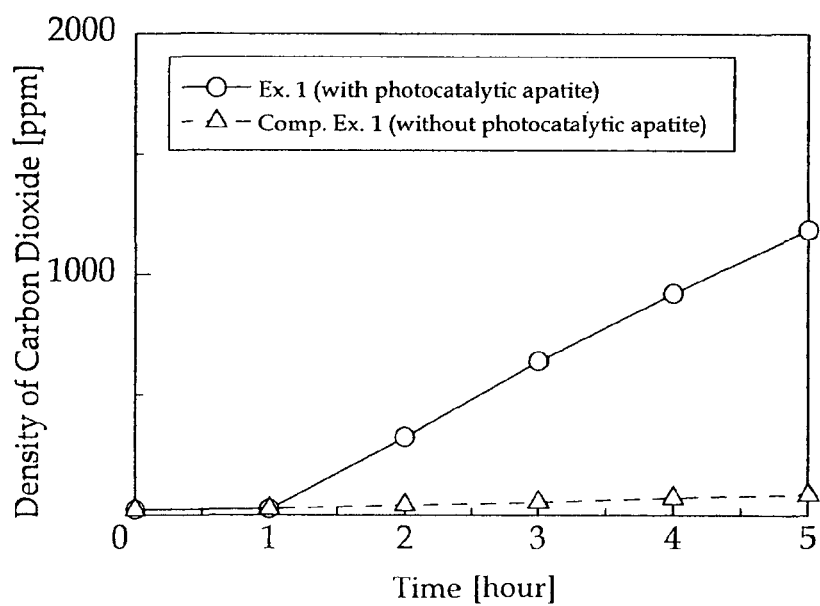
FIG. 2 is a graph showing a measurement result of photocatalytic activity of Example 1 of the present invention and Comparative Example 1 using a cotton fabric to which photocatalyst is not attached.

From the result shown in FIG. 2, a production of carbon dioxide was observed in the sample of Example 1, in which a cotton fabric formed with the photocatalytic fiber of the present invention was used, and it was confirmed that the acetaldehyde was decomposed and the sample had photocatalytic activity. On the other hand, carbon oxide was not produced in the sample of Comparative Example 1, in which a cotton fabric to which the photocatalyst is not attached at all was used, and the sample had no photocatalytic activity.

(3) <Evaluation of Fiber Degradation>

Each sample (in strip form of 25 mm×150 mm) of Example 1 and Comparative Examples 1 and 4 was put in a box for ultraviolet irradiation and 2.0 mW/cm² (at 365 nm) of ultraviolet light was continuously irradiated and tensile strength of each sample was measured after one month and three months of irradiation using a tensile testing machine manufactured by Instron Corporation. Results are shown in FIG. 3.

Figure 3:
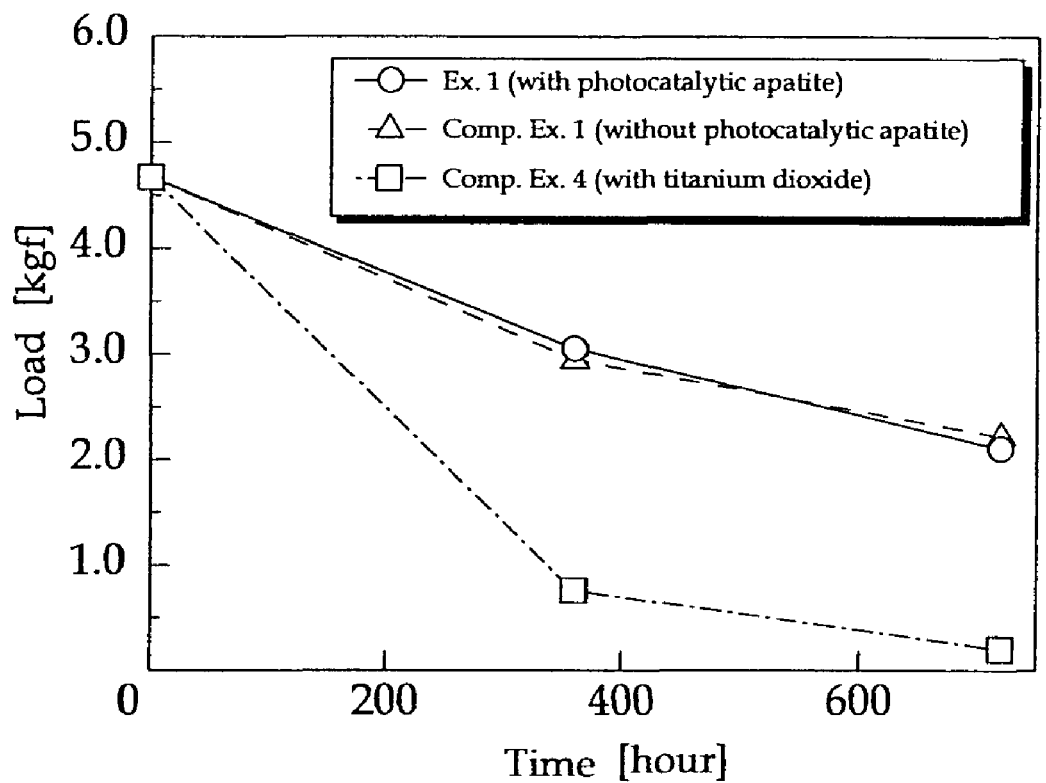
FIG. 3 is a graph showing a measurement result of the tensile test of Example 1 of the present invention, Comparative Example 1 and Comparative Example 4.

From the result shown in FIG. 3, the cotton fabric of Example 1, in which a cotton fabric formed with the photocatalytic fiber of the present invention was used, exhibited the same fiber strength as that of the sample of Comparative Example 1, in which the photocatalyst is not attached, even after ultraviolet irradiation, and the degradation of the fiber by photocatalyst was not observed. On the other hand, it turns out that the tensile strength of the sample of Comparative Example 4 to which a titanium dioxide was attached was notably degraded, thereby degrading the fiber.

By the present invention, it is possible to settle above existing issues and to provide the photocatalytic fiber which has an excellent durability and decomposition ability against harmful components such as harmful materials or disease agents contained in air, soil and water, and can be mass-produced at low cost. And by the use of the photocatalytic fiber, also provided is the fabric which excels in photocatalytic function and durability, and can be mass-produced at low cost. And by the use of the fabric, it is also possible to provide the fabric product including sanitary materials such as mask, medical cloth, bandage, and gauze, room decorative articles such as curtain, carpet and wall paper, clothing items such as uniform and clothes, livingwares such as towel, sheets and beddings and various filters, which is capable of exhibiting excellent photocatalytic function for prolonged period.

The photocatalytic fiber of the present invention is favorably used for fabric products including sanitary materials such as mask, medical cloth, bandage, and gauze, room decorative articles such as curtain, carpet and wall paper, clothing items such as uniform and clothes, livingwares such as towel, sheets and beddings and various filters, because the fiber has excellent durability and decomposition ability against harmful components such as harmful materials or disease agents contained in air, soil and water, and can be mass-produced at low cost.

The fabric of the present invention is favorably used for fabric products including sanitary materials such as mask, medical cloth, bandage, and gauze, room decorative articles such as curtain, carpet and wall paper, clothing items such as uniform and clothes, livingwares such as towel, sheets and beddings and various filters, because it is formed by using the photocatalytic fiber of the present invention and has excellent durability and decomposition ability against harmful components such as harmful materials or disease agents contained in air, soil and water and can be mass-produced at low cost.

The fabric product of the present invention is favorably used for sanitary materials such as mask, medical cloth, bandage, and gauze, room decorative articles such as curtain, carpet and wall paper, clothing items such as uniform and clothes, livingwares such as towel, sheets and beddings and various filters, because it is formed by using the fabric of the present invention and is capable of exhibiting excellent photocatalytic function for prolonged period.

What is claimed is:

1. A method for forming a photocatalytic fiber, comprising:
   dipping a fiber in a solution that comprises a photocatalyst so that the photocatalyst is attached to the fiber,
   spinning the fiber to form a thread to which the photocatalyst is attached, and
   dipping the thread to which the photocatalyst is attached in the solution that comprises the photocatalyst.

2. The method for forming a photocatalytic fiber according to claim 1, wherein the photocatalyst is in form of particle.

3. The method for forming a photocatalytic fiber according to claim 1, wherein the photocatalyst is capable of exhibiting photocatalytic activity at least by visible light.

4. The method for forming a photocatalytic fiber according to claim 1, wherein the photocatalyst comprises at least an apatite which comprises photocatalytic activity and a visible light-absorbing metal atom.

5. The method for forming a photocatalytic fiber according to claim 4,
   wherein the apatite comprises photocatalytic activity, and
   wherein the apatite comprises a metal atom and at least a part of the metal atom is substituted with the visible light-absorbing metal atom.

6. The method for forming a photocatalytic fiber according to claim 4, wherein the visible light-absorbing metal atom is chromium (Cr).

7. The method for forming a photocatalytic fiber according to claim 4, wherein the apatite comprises photocatalytic activity, and
   wherein the apatite comprises a metal atom necessary for obtaining photocatalytic activity.

8. The method for forming a photocatalytic fiber according to claim 7, wherein the metal atom necessary for obtaining photocatalytic activity is at least one selected from titanium (Ti), zinc (Zn), manganese (Mn), tin (Sn), indium (In) and iron (Fe).

9. The method for forming a photocatalytic fiber according to claim 4, wherein the apatite is expressed by the following General Formula (I):

$$A_m(BO_n)_z X_s \qquad \text{General Formula (I)}$$

where, in the above General Formula (I), "A" represents a metal atom, "B" represents any one of phosphorus atom (P) and sulfur atom (S), "O" represents an oxygen atom, "X" represents any one of hydroxyl group, $CO_3$ and halogen atom, "m" represents an integer of 8 to 10, "n" represents an integer of 3 to 4, "z" represents an integer of 5 to 7, and "s" represents an integer of 1 to 4.

10. The method for forming a photocatalytic fiber according to claim 9, wherein in the General Formula (I), "A" represents calcium (Ca), "B" represents phosphorus atom (P) and "X" represents a hydroxyl group, and the apatite comprising photocatalytic activity is calcium hydroxyapatite, $Ca_{10}(PO_4)_6(OH)_2$.

11. The method for forming a photocatalytic fiber according to claim 8, wherein the metal atom necessary for obtaining photocatalytic activity is titanium (Ti).

12. The method for forming a photocatalytic fiber according to claim 1, wherein the photocatalyst comprises an ultraviolet-absorbing metal atom.

* * * * *